_United States Patent_ [19]

Sterzer

[11] Patent Number: 4,632,127
[45] Date of Patent: Dec. 30, 1986

[54] SCANNING MICROWAVE HYPERTHERMIA WITH FEEDBACK TEMPERATURE CONTROL

[75] Inventor: Fred Sterzer, Princeton, N.J.

[73] Assignee: RCA Corporation, Princeton, N.J.

[21] Appl. No.: 745,181

[22] Filed: Jun. 17, 1985

[51] Int. Cl.⁴ .............................................. A61N 5/00
[52] U.S. Cl. .............................. 128/804; 219/10.55 R; 219/10.55 F; 374/121
[58] Field of Search ................ 128/804, 399, 736, 783, 128/422; 374/122, 124, 121; 343/351, 720; 219/10.55 R, 10.55 F

[56] References Cited

U.S. PATENT DOCUMENTS

| | | | |
|---|---|---|---|
| 2,549,399 | 4/1951 | Tawney | 219/10.81 |
| 3,457,924 | 7/1969 | Kendall | 128/404 |
| 3,800,802 | 4/1974 | Berry et al. | 128/422 |
| 3,924,196 | 12/1975 | Takahashi et al. | 328/253 |
| 3,978,864 | 9/1976 | Smith et al. | 128/404 |
| 4,190,053 | 2/1980 | Sterzer | 128/399 |
| 4,197,860 | 4/1980 | Sterzer | 128/804 |
| 4,228,809 | 10/1980 | Paglione | 128/804 |
| 4,230,129 | 10/1980 | LeVeen | 128/804 |
| 4,271,848 | 6/1981 | Turner et al. | 128/804 |
| 4,341,227 | 7/1982 | Turner | 128/804 |
| 4,346,716 | 8/1982 | Carr | 128/653 |
| 4,397,314 | 8/1983 | Vaguine | 128/399 |
| 4,434,341 | 2/1984 | Busby | 219/10.55 |
| 4,448,198 | 5/1984 | Turner | 128/422 |
| 4,471,787 | 9/1984 | Bentall | 128/804 |

FOREIGN PATENT DOCUMENTS

| | | | |
|---|---|---|---|
| 3048682 | 9/1981 | Fed. Rep. of Germany | 128/804 |
| 0203686 | 11/1983 | Fed. Rep. of Germany | 128/804 |
| 1045546 | 10/1966 | United Kingdom | 128/804 |
| 2165428A | 4/1986 | United Kingdom | |

Primary Examiner—Lee S. Cohen
Attorney, Agent, or Firm—Joseph S. Tripoli; Robert L. Troike; William H. Meise

[57] ABSTRACT

An electromagnetic or microwave hyperthermia method includes an antenna and a noncontacting temperature sensor such as an infrared sensor or a radiometer which together scan a predetermined path over the surface of tissue to be treated. The temperature sensor senses temperature of the tissue, and a controller closes a feedback loop which adjusts the microwave power applied to the antenna in a manner which raises the temperature of the tissue uniformly. An apparatus for accomplishing the method includes an X-Y controller which scans a rectilinear path over the patient or a portion thereof, carrying a loop antenna oriented with its axis normal to the surface to be heated. A noncontacting temperature sensor is carried coaxially aligned with the loop to prevent erroneous temperature indications as the distance of the antenna and temperature sensor assembly from the patient varies. A controllable attenuator is coupled between a microwave generator and the antenna. A controller responsive to the temperature sensor and to a preset temperature adjusts the attenuator in a feedback manner to establish a preselected uniform temperature.

14 Claims, 12 Drawing Figures

SCANNING MICROWAVE HYPERTHERMIA WITH FEEDBACK TEMPERATURE CONTROL

BACKGROUND OF INVENTION

This invention relates to hyperthermia therapy in which the temperature of living tissue is increased for therapeutic purposes, and particularly to apparatus and method for microwave hyperthermia treatment.

Hyperthermia treatments have for many years been used for treatment of cancers. It is known that raising of the temperature of cells to above about 43° to 45° C. for sufficient time causes necrosis, and temperatures below about 41.5 generally do not affect cells. Some types of malignant cells reportedly can be destroyed by raising their temperatures to levels slightly below those injurious to most normal cells. One of the techniques which has been used for hyperthermia is heating of the blood of a patient by an external apparatus, thereby raising the temperature of the entire body or a portion thereof to the therapeutic temperature. This procedure risks substantial injury to the patient if temperature is not carefully controlled, and may fail to raise the temperature of the malignant cells sufficiently for destruction. Any malignant cells which remain undestroyed may cause a recurrence of the tumor, growth or malignancy (hereinafter tumor).

Some surface tumors may be successfully treated by application of surface heat from a heated object. Deeply located tumors, however, are difficult to heat to therapeutic temperatures without destruction of the overlying tissue.

Another hyperthermia technique uses electromagnetic radiation to heat tissue. The electromagnetic radiation is often in the form of radio frequency (RF) or microwave radiation because of the ease of generating, controlling and directing microwaves, and also because of the absorption characteristics of tissue at microwave frequencies. At the current state of the art, microwave hyperthermia is usually at frequencies in the range of 100 MHz to 5 GHz. Microwave hyperthermia when applied to tissue containing a tumor generates heat within the tissue which raises the temperature of the tissue generally. It has been found that tumors tend to have a limited blood supply by comparison with healthy tissue. Thus, the circulation of blood through a tumor is low by comparison with circulation through healthy tissue. At any microwave power density, the tumor will usually be hotter than the surrounding healthy tissue because the more ample flow of blood in the healthy tissue provides cooling of the healthy tissue. Thus the tumor may be heated by microwave hyperthermia to a therapeutic temperature without significant effect on surrounding healthy tissue.

It has been found that microwave hyperthermia when used in conjunction with either radiotherapy or with chemotherapy provides more consistent success than either alone. A course of treatment may include several radiotherapy treatments each week, interspersed with microwave hyperthermia treatments. Widespread practical application of such combined therapy depends upon the availability of convenient and predictable microwave hyperthermia methods and apparatus.

U.S. Pat. No. 4,448,198 issued May 15, 1984, to Turner describes an invasive hypertherapy arrangement in which a plurality of microwave applicators are inserted into body tissue. The surgical implantantion requires the use of an expensive operating room and the services of a skilled surgeon, which is not convenient. The applicators provide numerous potential sites for infection and at least require care by the patient. The implanted applicators may interfere with concurrent radiotherapy. Since the dielectric constant of the tumor may differ from that of the surrounding tissue, the energy from the microwave applicators may be partially reflected by the tumor if the applicators are implanted in healthy adjacent tissue, and this may result in an undesirable temperature distribution.

Noninvasive microwave hyperthermia relies upon heating from applicators placed outside the patient's body. This is particularly convenient for small surface tumors, the extent of which can be readily seen. The applicator is often held in contact with the surface being treated to avoid excessive spreading of the energy. For small tumors, a single applicator may be used. The center of the applicator is directed towards the tumor, and the power is applied. Adjacent normal tissue is likely to be at a lower temperature than the temperature at the tumor because a simple applicator such as a horn has a power distribution which decreases away from the center or axis. The temperature of the tumor may be monitored by a small sensor inserted into the tumor. However, if the temperature sensor is electrically conductive it may itself be heated, thereby providing an erroneous indication that the tumor is being heated Also, the electrically conductive temperature sensor may perturb the field, for example by signal reflection, and therefore cause constructive interference at a location away from the axis of the application. This may undesirably damage normal tissue. If the probe is thermally conductive it may undesirably cool the tumor.

Large tumors are more difficult to treat. When an applicator such as a horn with a single aperture is used, the power distribution across the aperture of the applicator may heat the center of the area to too high a temperature, and thereby cause burning, or may not heat outlying portions of the tumor to therapeutic temperatures. Failure to sufficiently heat portions of the tumor allows regrowth of the tumor. Burned areas subject to radiation therapy tend to heal slowly or not at al. Ordinarily, radiation therapy is discontinued if the area to be irradiated is injured. Any burning of a part of the tumor by microwave hyperthermia is therefore undesirable, as it may limit therapeutic options. Other variables include surface phenomena such as reduction of surface temperature by perspiration, reflection of microwave energy by bone structures, and the use of heating or cooling pads applied to the surface being treated. A major cause of temperature differences is variation of blood flow to various portions of the tissues being heated. Thus, the treatment of large tumors presents difficulties not found in small tumors.

One known technique for hyperthermia treatment of large tumors is to use a "blanket" applicator which is large enough to cover the entire area to be treated. Such large area applicators are ordinarily made up of an array of a number of relatively small antennas. While such an applicator is theoretically plausible, there are practical difficulties. Since the antennas are spaced one from another on the blanket, those portions of the surface to be treated which lie immediately under an antenna element receive substantially more power than those areas lying between antenna elements and therefore tend to be heated more than outlying areas. Attempts to improve the power distribution by phasing the antennas (as in the Turner patent) to provide constructive reinforcement of the hyperthermia energy at points between antenna elements often fail. The failure comes about because the effective path length of the hyperthermia power passing through a dielectric medium depends upon the dielectric constant of the medium. When the medium is tissue, the dielectric constant varies from point to point and also depends upon the type of tissue (fat, muscle, etc.) through which the field passes. This results in a relatively random distribution of heating, and in the occurrence of hot spots at which burning of the tissue may occur, and also in cold spots at which therapeutic temperatures are not obtained. Such burns may not be visible and may undesirably remain unhealed for long periods if concurrent radiotherapy takes place.

An applicator for providing a uniform microwave field over a relatively large area is described in U.S. Pat. No. 4,271,848 issued June 9, 1981, to Turner. Ideally, such a field should provide uniform heating of a region of tissue. The heating effect will not be uniform, however, because of differences in the amount of absorption of power from the field by various different types of tissue. Even assuming that the heating attributable to the applicator is uniform over the surface to be treated, therapeutic results are not likely to be optimum, because of differences in the vascularization (number and size of bood vessels) and blood flow of various portions of the tissue or surface being heated. A plentiful supply of blood vessels and plentiful supply of blood to one portion of the tissue may result in much lower equilibrium temperatures during hyperthermia than an adjacent area with a paucity of blood vessels and poor supply of blood. Thus, the combination of uneven heating of the tissue by the applicator and of variable amount of cooling by the blood supply results in widely varying temperatures across the surface or throughout the tissues being treated.

A method for treating large tumors is described in U.S. Pat. No. 4,397,314 issued Aug. 9, 1983, to Vaguine. This technique implants temperature sensors in the tumor and in the surrounding tissue. A microwave generator under control of the temperature sensors is coupled to a plurality of external applicators and controls the energy applied to each applicator to provide therapeutic temperatures inside the tumor with an overriding protection of the surrounding healthy tissue. Individual microwave applicators are evaluated during the hyperthermia treatment to determine their effect on the overall heating pattern for optimizing the heating pattern. Besides being invasive, this arrangement has the disadvantage that implanted temperature sensors may have to be moved during the course of the treatment as the tumor size is reduced and healthy tissue replaces it. Since the size of the tumor and the physiological condition of the patient change during the course of the therapy, the optimization of the applicators must be done anew during each session of therapy. This is labor-intensive, and the optimization is subject to human error.

SUMMARY OF THE INVENTION

A hyperthermia method by mechanically scanning an antenna and a noncontacting temperature sensor together along a predetermined path over the surface of that portion of the patient to be treated. The amount of electrical signal coupled to the antenna is controlled in response to the temperature sensed to maintain a predetermined temperature. An apparatus which may be used to perform the method includes an antenna and a noncontacting temperature sensor mounted on a mechanical scanner controlled to make recurrent scans in a predetermined path over the patient. The electrical signal or power from a generator is applied to the antenna by way of a controllable attenuator. The attenuator is controlled by a controller in response to a comparison of a signal from the temperature sensor and a reference signal representing the desired temperature.

DETAILED DESCRIPTION OF THE INVENTION

Figure 1:
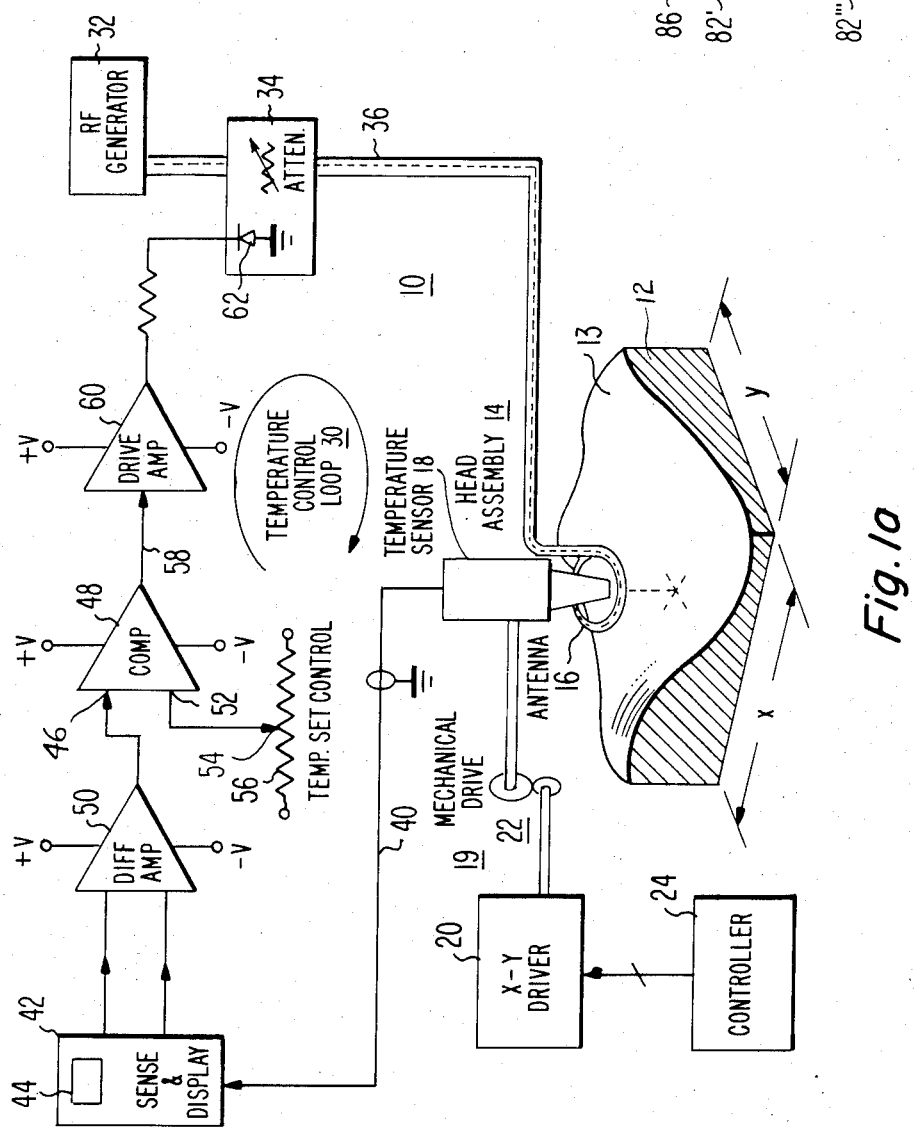
FIG. 1a is a diagram, partially in block and partially in pictorial from, of a hyperthermia apparatus according to the invention.
FIG. 1b illustrates a rectilinear scanning path.

FIG. 1a illustrates an apparatus according to the invention. In FIG. 1a a portion of tissue to be treated by hyperthermia is designated as 12 and has a skin surface 13. A scanning head assembly designated generally as 14 including an antenna 16 illustrated as a loop and a noncontacting temperature sensor 18 is mechanically scanned over the surface of tissue portion 12 by an X-Y driver 20 and mechanical drive 22 designated together as mechanical scanner 19. The scanning path over which the scanning head assembly 14 is driven is controlled by a controller 24. Within the limits of mechanical drive 22, controller 24 may preselect any portion of the tissue for scanning. As illustrated in FIG. 1a, the scanning range is illustrated by dimensions x and y. The rectilinear scanning path is illustrated in FIG. 1b, together with the x-y limits established by controller 24. As illustrated, the scanning path includes a plurality of scans 80, 80', ... 80''' separated by steps 82, 82', 82'' ... 82''' for stepping the antenna from one scan position to the next scan position. At the end of scan 80''', the antenna assembly returns from end position 84 to starting position 86 along a path 88, to begin another scan. Thus, antenna assembly 14 is scanned relatively rapidly over the surface in close proximity to, but not touching, the surface being treated.

Antenna 16 and temperature sensor 18 are coupled to a temperature control loop designated generally as 30. Antenna 16 receives power from an electrical signal generator or radio frequency power generator 32 by way of a controllable attenuator 34 and a transmission line 36. The power produced by generator 32 is selected to be great enough to provide more than the required amount of power for hyperthermia treatment of surface tissue portion 12. Attenuator 34 is controlled by temperture sensor 18 in a feedback manner by temperature control loop 30 so as to provide moment-to-moment or instantaneous control of the amount of power flowing from generator 32 to antenna 16 to compensate for variations from point to point in the vasculature of tissue portion 12 and for variations in the absorption of energy from the antenna field by the various types of tissue which may be encountered in tissue portion 12. As mentioned above, such variations from point to point in the absorption and in the amount of cooling would prevent a uniform temperature in tissue portion 12 if the amount of electrical power applied from point to point were uniform.

Feedback loop 30 includes noncontacting temperature sensor 18, which produces a signal on conductor 40 representative of the instantaneous temperature of the tissue portion heated by antenna 16. The temperature indicative signal is applied to a temperature sensing and display electronics illustrated as a block 42 which includes a readout 44 for displaying the indicated temperature. Sensing and display electronics 42 also produces an output signal which is representative of the temperature sensed by sensor 18 which is applied to an input terminal 46 of a difference amplifier or comparator 48 by way of a differential amplifier 50. Comparator 48 compares the signal applied to input terminal 46 with a reference signal applied to input terminal 52 which represents the temperature to which the surface tissue portion 12 is to be raised. As illustrated, the desired temperature setting is derived from a tap 54 on a potentiometer 56 coupled to an appropriate power supply (not illustrated). Comparator 48 produces a control signal on a conductor 58 which is applied to an attenuator drive amplifier 60 for driving the active portion, illustrated as a PIN diode 62, of attenuator 34. PIN diode attenuators are known in the art. Temperature control loop 30 variably attenuates or reduces the amount of power flowing from generator 32 to antenna 16 moment by moment during the scanning of head assembly 14 over tissue portion 12 in order to maintain the desired temperature.

In a particular embodiment of the invention, the mechanical scanner 19 is a commercially available Hewlett-Packard Model 9872A x-y plotter. This computer controlled mechanical arm 19 can move the assembly 14 to any location within a 28×40 cm rectangular field. This plotter is compatible with a Model 85 Hewlett-Packard computer, also commercially available, and the combination is capable of large numbers of predetermined motions, one of which is illustrated in FIG. 1b.

In one embodiment of the invention, temperature sensor 18 is the sensing head of a model C-600M biotherm noncontacting infrared thermometer manufactured by Linear Laboratories, a Division of Linear Corporation, 445 South San Antonio Road, Los Altos, Calif. 94022. This instrument has a temperature range of 10° to 50° C., a sensitivity of 0.1° C. and an accuracy of 0.5° C. The target diameter is 0.25"(0.6 cm) at 0.75" (1.9 cm). The infrared sensor used in the C-600M is optically filtered to limit the response of the instrument to the infrared spectral band from 8 to 14 microns. This head senses temperature at and near the surface 13 of tissue portions 12 with a speed of response of about 1/10 of a second. The circuit portions 42 of the C-600M produce an output signal which changes one millivolt per degree centigrade of indicated temperature. Because of the fast response of the temperature sensor and of the remainder of control loop 30, relatively uniform temperatures are achieved in the tissues being treated.

Figure 2:
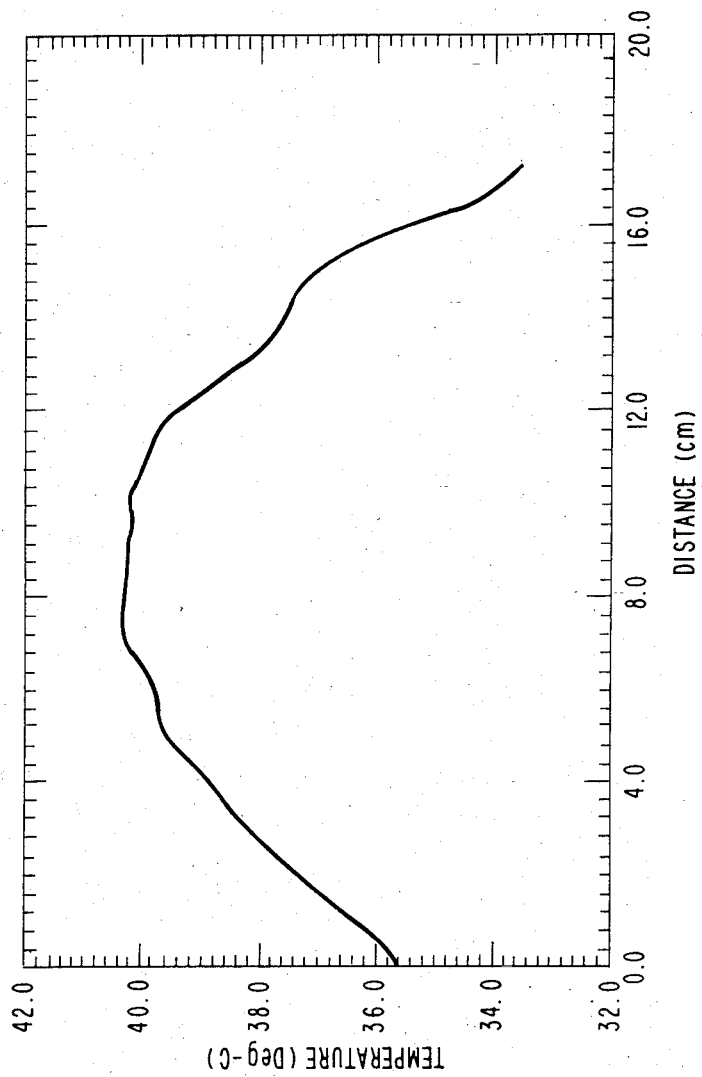
FIG. 2 is a plot of surface temperature versus position along a path over the surface of part of the thigh muscle of a dog after hyperthermia performed according to the invention.

In a particular embodiment of the invention, generator 32 operated at a frequency of 2450 megahertz (MHz) with a power of 100 watts. In a particular test, the antenna and temperature sensor assembly 14 was scanned in a pattern as illustrated in FIG. 1b over a rectangular area having an x dimension of 7.62 cm and a y dimension of 7.62 cm, broken into 4 transverse scans 82 each having a length of 19.05 mm. The antenna 16 of head assembly 14 was typically one to two cm above the treatment area. Separate tests were conducted with the apparatus as so far described on the thigh muscle of a dog and on a muscle equivalent phantom consisting of 68% $H_2O$, 30% gelatin, 1% NaCl, and 1% Formalin. The time required for one complete scan over the area being treated was 11 seconds. After heating was completed by recurrent scans, surface temperatures were measured with the infrared sensor in steps at points separated by 6.35 mm along an x scan lying in the center of the area treated. A maximum temperature rise of 7.8° C. uniform to within ±0.25° C. was obtained on the muscle equivalent phantom over a length of 4.2 cm of the center of the x scan. FIG. 2 is a plot of the surface temperature along a centered x scan after the heating of the thigh muscle of a dog. The temperature is within ±0.1° C. over a length of 4.4 cm.

Figure 3:
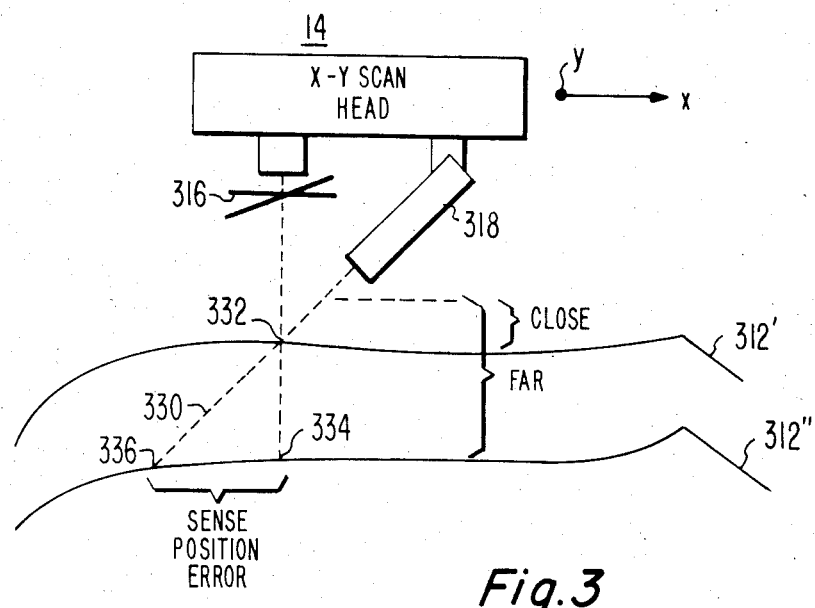
FIG. 3 illustrates a source of error in temperature sensing.

FIG. 3 illustrates a problem which can occur when performing an x-y scan as described in conjunction with FIG. 1a when the antenna, (illustrated as a crossed dipole 316) is offset from the field of view axis 330 of the temperature sensor, illustrated as 318. Tissue portion 312 is illustrated in two positions, a close position 312' and a relatively remote position 312". When axis 330 of the field of view of temperature sensor 318 intersects surface 312' relatively close to antenna 316, surface 312' receives maximum heating from antenna 316 at a position 332 on surface 312'. Position 332 corresponds with the position being viewed or monitored by temperature sensor 318, and therefore the feedback control of temperature will attempt to control the temperature at point 332 to the desired temperature. When tissue portion 312 is in position 312" somewhat more distant from antenna 316, the point on surface 13 receiving the maximum amount of power from antenna 316 corresponds to point 334 on surface 312". The position being viewed by sensor 318, however, is position 336 at the intersection of axis 330 and surface 312". This position does not correspond to the position receiving the maximum amount of energy, so the feedback loop will attempt to control the power applied to antenna 316 in order to maintain point 336 at the desired temperature. This will result in points corresponding to 334 being raised to excessively high temperature. This is undesirable, for reasons described above.

Figure 4:
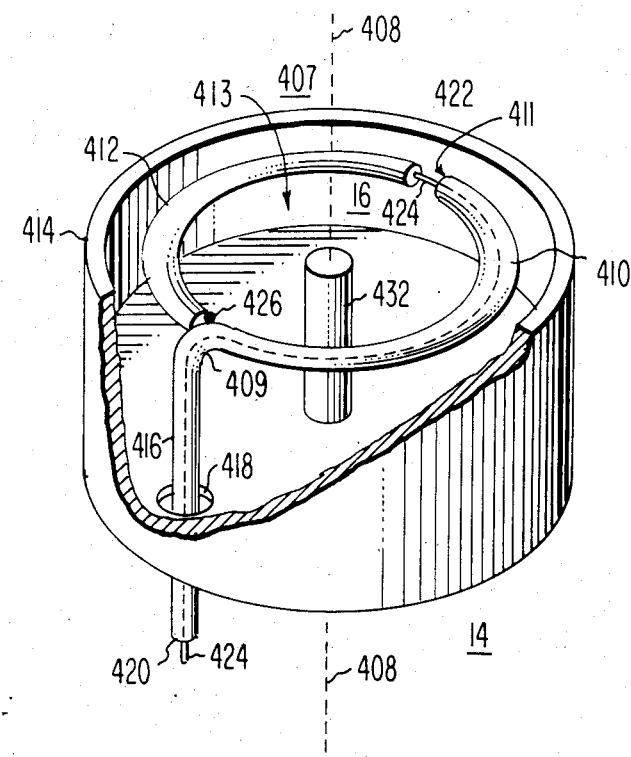
FIG. 4 is a simplified isometric view of the antenna and temperature sensor assembly illustrated in FIG. 1, partially cut away to illustrate the interior.

FIG. 4 illustrates in simplified form the arrangement of the antenna 16 and temperature sensor 18 in scanning head assembly 14. Basically, antenna 16 consists of a loop or convolution designated 407 formed by a first elongated conductive element 410 formed into a semicircle and a second elongated conductive semicircular element 412 formed into a complementary semicircle, with a small gap therebetween in a feed region gap designated generally as 422. Such loop antennas are well known in the art. Major differences among various loop antennas include the method of applying feed signal across feed point or gap 422 for energizing the loop, and in the method for supporting the loop. As illustrated in FIG. 4, a cavity 413 is defined by a conductive housing 414 and a loop 407 is supported at the opening of cavity 413 by a portion 416 of rigid coaxial cable (coax) having an outer conductor 420 and a center conductor 424. Coax portion 416 passes through and is in turn supported at an aperture 418 in the closed end of cavity 413. In order to feed signals to feed gap 422 of loop 407, conductive semicircular element 410 is formed as the outer conductor of an extension of coax portion 416, extending from a right angle bend at a location 409 to feed gap 422. In order to clearly differentiate the conductive outer portion of the outer conductor from the coaxial transmission line within portion 410, the coaxial portion within conductive loop portion 410 is designated 411. Coaxial cable portion 416 receives the hyperthermia electrical signals at its input end 420 and couples them past bend 409 and through the interior portion 411 of semicircular coaxial element 410 to loop feed gap 422. At feed gap 422 loop portion 410 ends, and its inner coaxial portion 411 also ends. The center conductor 424 of coax portion 411 passes across gap 422 and connects to solid semicircular conductive loop 412. This arrangement drives the ends of conductive elements 410 and 412 near feed point 422 with mutually out-of-phase signals. The end of semicircular loop portion 412 remote from feed gap 422 is electrically connected to the outer conductor 420 of coaxial element 416 at bend 409 as by a solder connection illustrated as 426. This creates planar conductive loop 407 including conductive portions 410 and 412, interrupted only by gap 422.

When the dimensions of loop antenna 16 are relatively small by comparison with a wavelength at the frequency of the applied electrical signal, the mutually out-of-phase drive signals at feed gap 422 create currents around the loop which are in the same circumferential direction and relatively uniform in their magnitude. Under these conditions, the magnetic fields are directed generally in the direction of axis 408 in the region within loop 16. Variations in magnetic flux due to the loop drive signal do not cause a magnetic flux which crosses (is at right angles to) the length of portion 432 of probe sensor 18. The variation of magnetic flux causes a variation of intensity of that portion of the magnetic field coaxial with probe portion 432, which produces relatively little interaction between the probe and the magnetic field. Because of the low impedance of the relatively short loop, the electric field intensity is relatively low and tends to cancel near central axis 408. Thus, the theorical field intensity on axis 408 is low, and the field distribution is not perturbed by introduction of a metallic object such as a portion 432 of remote temperature sensing element 18. The field of view of temperature sensor 18 coincides with axis 408.

Because the currents around the loop are equal in magnitude, as mentioned above, the current on half-loop 410 equals the current on half-loop 412. Consequently, at bend 409, the current leaving portion 410 equals the current entering portion 412. There is no current difference which can flow on the outside of the outer conductor 420 of coax 416, and coax 416 is therefore electrically invisible.

Figure 5:
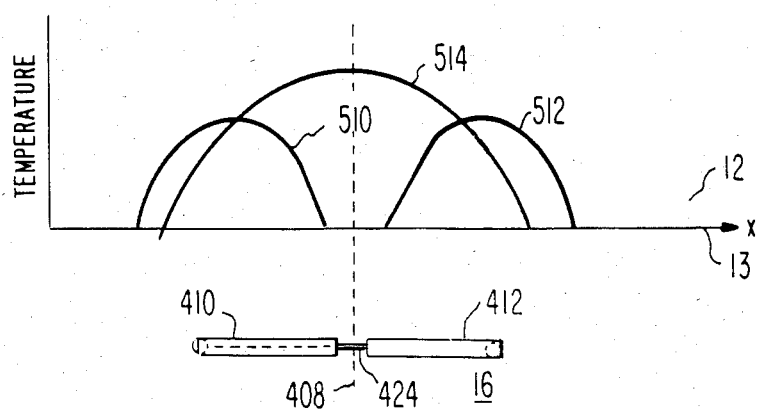
FIG. 5 is a plot of field distribution and heating for an antenna such as that illustrated in FIG. 4.

FIG. 5 illustrates as lobes 510 and 512 the heating or temperature variations which might be expected at surface 13 of tissue portion 12 along a line passing directly under antenna 16 due to the fields near conductors 410 and 412 of loop 407. Thus, one might expect that a loop antenna such as 16 would not provide as much heating in the tissue portion centered on axis 408 directly under the antenna as at points directly under the conductive loop elements. However, in practice the heating effect appears to be a single lobe such as lobe 514 centered on antenna axis 408.

Figure 6A:
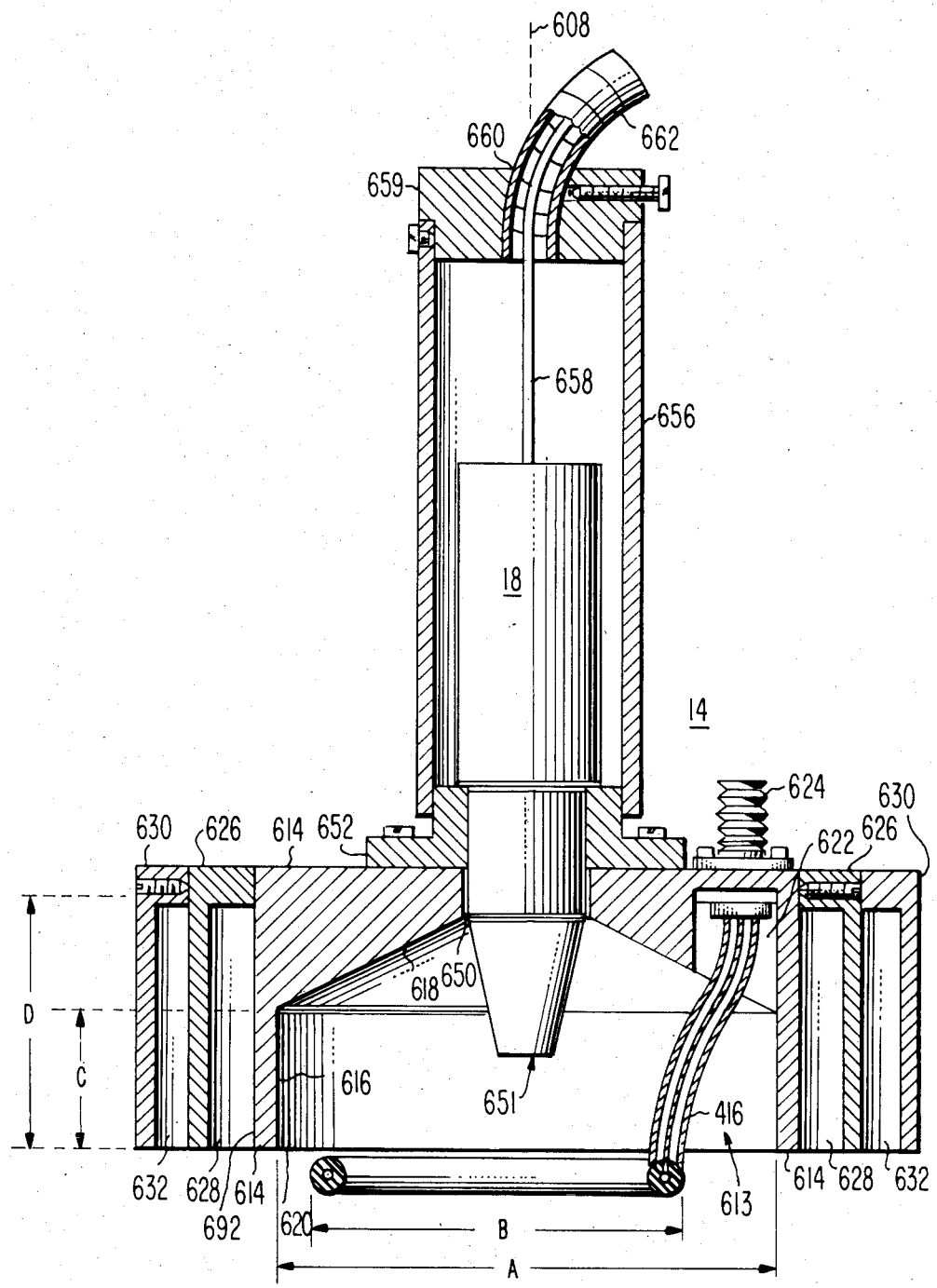
FIGS. 6a, b and c are more detailed cross-sectional, end and exploded views of the assembly of FIG. 4.
Figure 6B:
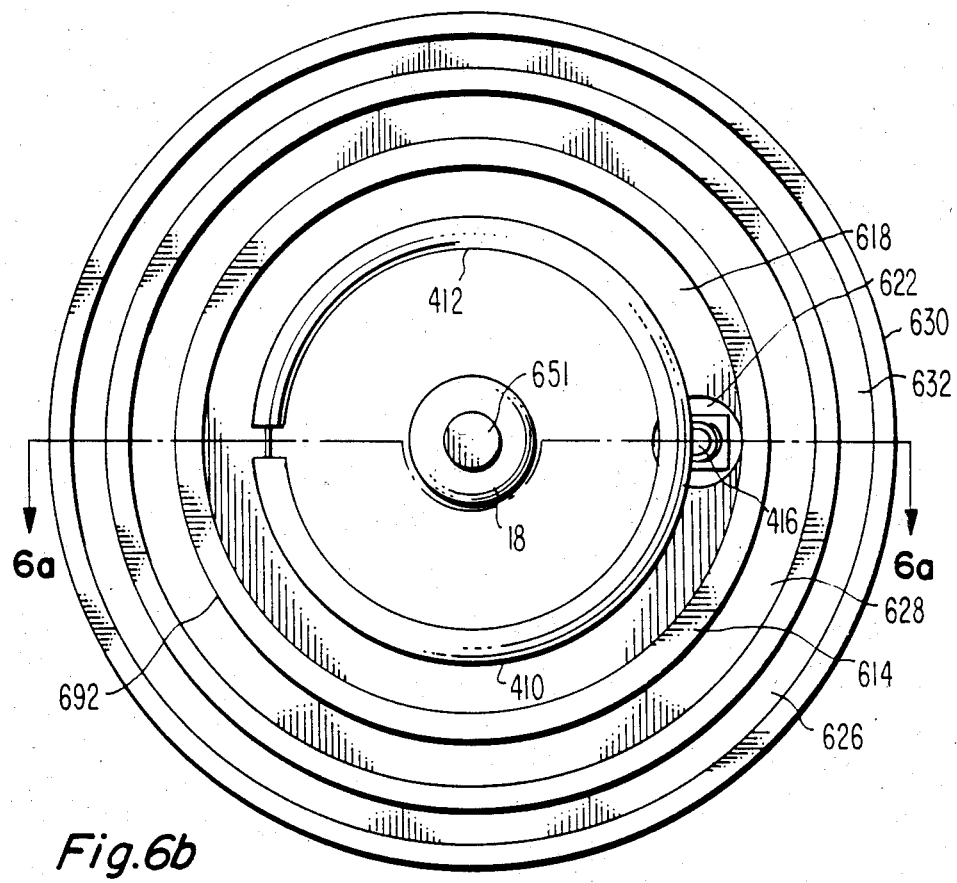
Figure 6C:
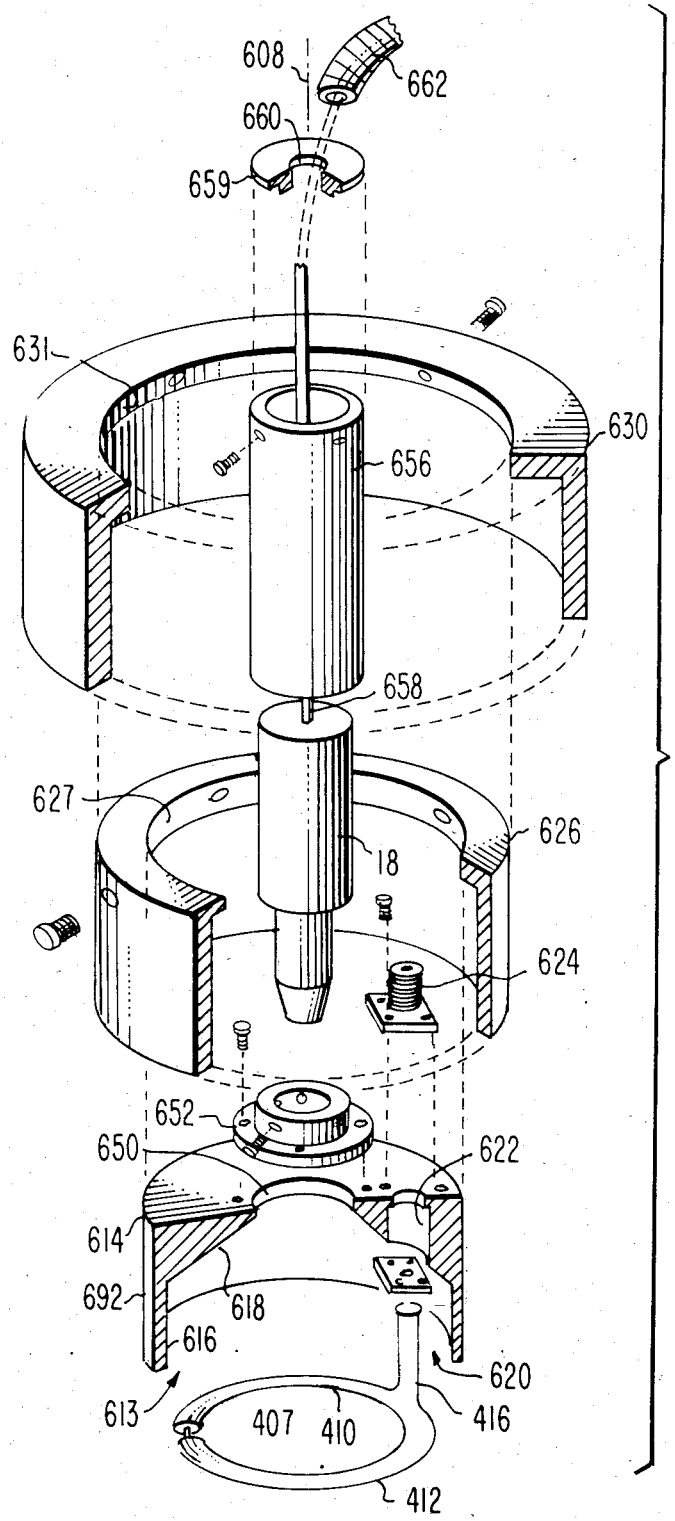

FIG. 6a illustrates in cross-sectional elevation view details of the antenna 16 and temperature sensor 18 of head assembly 14. FIG. 6b is an end view of the structure looking into the side facing the tissue being heated, and FIG. 6c is an exploded view. In FIGS. 6a, b and c a conductive cavity designated generally as 613 is defined by a housing 614 which includes a straight sided figure of revolution portion 616 and a tapered figure of revolution portion 618. Portions 410 and 412 of the loop antenna are located just outside the aperture 620 of the cavity. Coaxial conductor 416 supports the loop antenna including portions 410 and 412. Coax 416 passes into a hole 622 drilled part way through tapered portion 618 of housing 614 and is attached in known fashion to a bulkhead connector 624 which couples the hyperthermia signal from the outside of housing 614 to feed coax 416. Connector 624 provides electrical access to the loop antenna from the side of housing 614 facing away from the patient. During scanning operation, connector 624 is connected to flexible coax cable 36 (FIG. 1). A first conductive annular ring 626 defines an opening 627 which fits tightly around the outer edge of housing 614 and together with outer surface 692 of housing 614 forms an annular radio frequency (RF) choke defined by an annular cavity designated 628 which reduces leakage of energy from the antenna 16 and cavity 613 in directions other than towards the patient. A similar but larger annular ring 630 defines an opening 631 which fits tightly around the outer periphery of ring 626 and forms a second RF choke defined by an annular cavity designated 632 for further reduction of lateral energy leakage. The lengths of cavities 628 and 632 in a direction parallel to axis 608 are selected as known in the art to be approximately one quarter wavelength at the frequency of the electrical hyperthermia signal. As illustrated, cavity housing 614 defines a circular central aperture 650 through which the temperature sensing head or probe 18 of the aforementioned C-600M non-contacting infrared thermometer can protrude, with an aperture 651 in the end of probe 18 for the entry of temperature-representative radiation facing through the center of loop 407. A flange 652 affixed to the rear of cavity housing 614 clamps sensing head 18 firmly in place and provides electrical contact to the metallic portions of sensing head 18 to prevent leakage of residual electromagnetic signal through aperture 650. A support tube 656 is firmly clamped around flange 652 to support head assembly 14 and also to provide protection for sensing head 18. The temperature signals produced by sensing head 18 are conducted by a conductor set 658 to electronics 42 (not illustrated in FIGS. 6a, b or c). The upper part of support tube 656 is closed by a second flange 659 which includes a central aperture 660 for receiving a protective tube 662. Tube 662 is a conductive flexible tube such as flexible conduit (well known as the outer metallic sleeve of common BX house wiring cable for example). Inside the tube 662 is a rubber tube (not illustrated in FIG. 6) through which conductor set 658 passes. The rubber tube provides protection against pinching of conductor set 658 by flexing of the sections of flexible tube 662 during scanning. In normal operation, tube 656 is clamped to the movable arm portion of the x-y plotter by means of a clamping arrangement (not illustrated). The previously mentioned flexible coaxial cable 36 is coupled to coaxial connector 624 to provide power to antenna 16 from attenuator 34, and conductor set 658 is coupled to electronics 42 to provide temperature sensing for control of the power, all as described in conjunction with FIG. 1.

In the particular embodiment of the invention producing the results described in conjunction with FIG. 2, coax 416 and elements 410 and 412 of loop antenna 16 are formed from 0.141" (3.58 mm) "semi-rigid" coaxial transmission line. For operation at 2450 megahertz, cavity diameter A is 3.450" (8.76 cm), loop dimension B is approximately 1.35" (3.43 cm), cavity dimension C is 0.984"(2.49 cm), and choke depth D is 1.204" (3.06 cm).

As described in conjunction with FIG. 1 the mechanical scanning of the antenna and temperature sensor array is established by controller 24 over a portion of maximum scanning field available from driver 20 and mechanical drive 22. This requires that for each use of the apparatus, limits on dimensions x and y be set by the controller. It may be desirable to allow the mechanical scanner to always scan the maximum area of which it is capable, and to adjust the reference temperature so as to apply power to the antenna only over that portion of the total scanning area to be treated.

Figure 7:
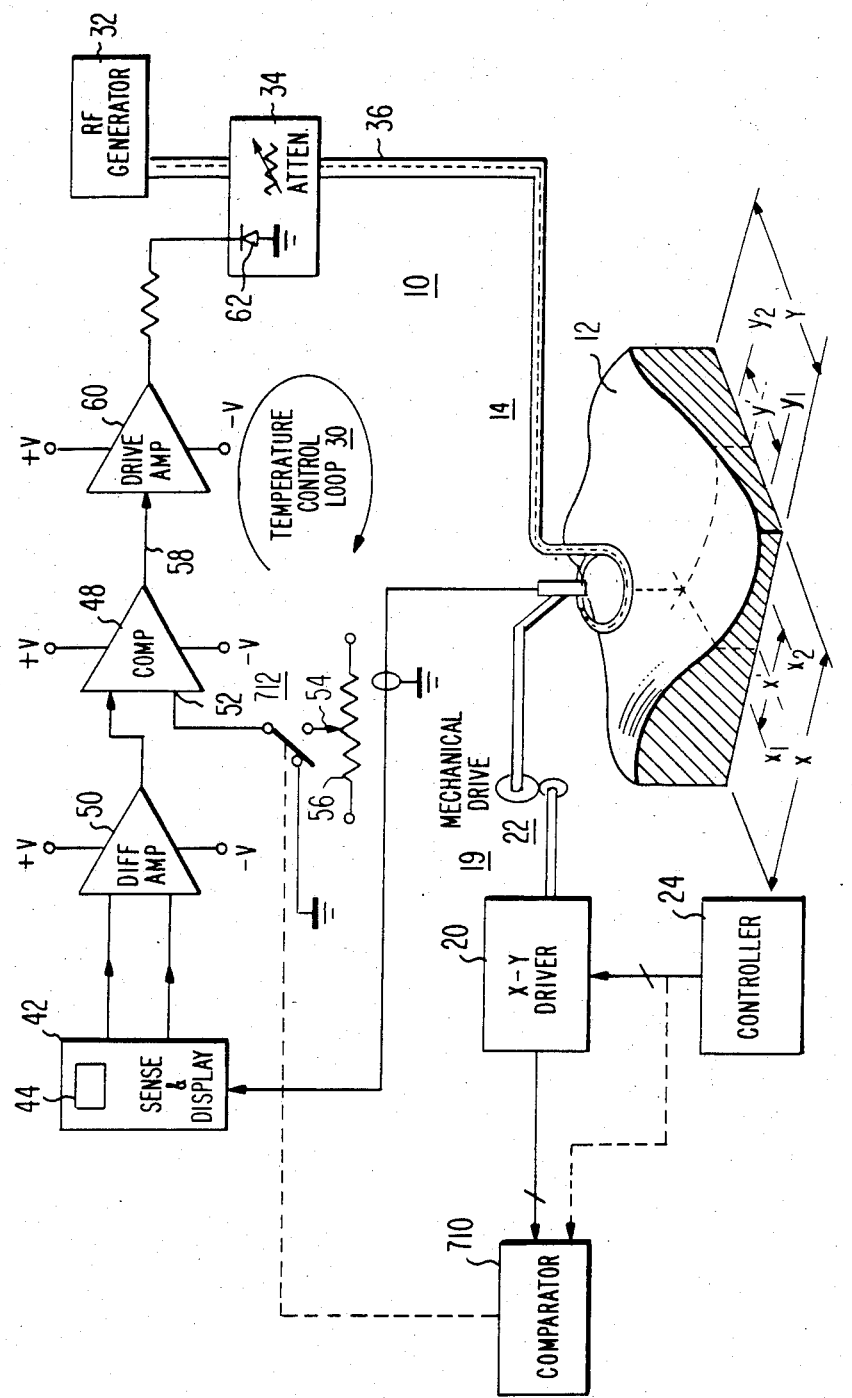
FIGS. 7 and 8a are diagrams, partially in block and partially in pictorial form, of other embodiments of the invention, and, FIG. 8b illustrates a scan pattern associated with FIG. 8.

As illustrated in FIG. 7, driver 20, mechanical drive 22 and controller 24 are set to drive assembly 14 over an area within limits illustrated as X and Y. It is desired to apply therapeutic values of temperature to tissue portion 12 in the region defined by the interval $x'$ lying between $x_1$ and $x_2$ and the interval $y'$ defined by the region between $y_1$ and $y_2$. This may be readily accomplished by applying to a comparator 710 digital signals from driver 20 representing the present location of scanning head 14 and comparing the digital signals with signals representing the desired values of $x_1$ and $x_2$, $y_1$ and $y_2$. The output of comparator 710 is an ON-OFF signal which is applied to a switch 712 which switches input terminal 52 of comparator 48 between ground and tap 54 of temperature set control 56. Thus, temperature control loop 30 controls the power flowing from generator 32 within the region bounded by $x_1$, $x_2$, $y_1$ and $y_2$ to establish therapeutic temperatures, and when the scanning head is outside that region, reduces the power to zero.

Figures 8A, 8B:
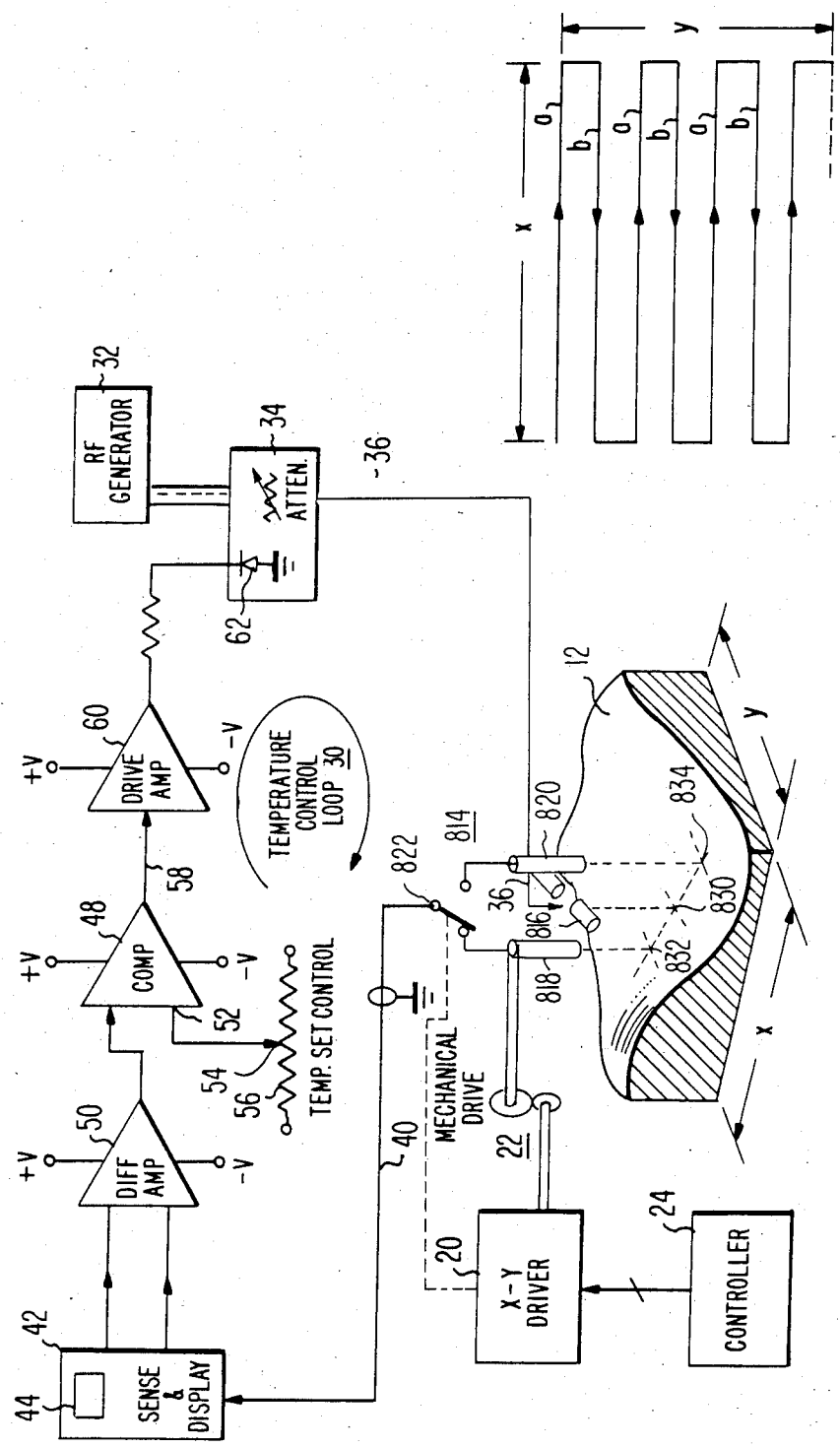

FIG. 8a illustrates an arrangement for those situations in which the temperature sensing element cannot be on the main axis of the antenna. As illustrated in FIG. 8a scanning head 814 includes a dipole antenna 816 fed by cable 36. The region heated by antenna 816 is illustrated as point 830. Two temperature sensors, 818 and 820, are located adjacent antenna 816 on opposite sides in the x direction. Thus, when the mechanical motion of mechanical drive 22 transports assembly 814 including antenna 816 and sensor 818 and 820 to the right in the x direction as illustrated in FIG. 8a, sensor 820 is looking at point 834 in an area which is not yet been heated, and sensor 818 is looking at a point 832 in the area of tissue portion 12 which has just been heated. Consequently, switch 822 controlled by a direction-of-scan signal from driver 20 is switched to a position which selects signal from sensor 818 for application to circuits 42 for control of temperature by means of control loop 30. Thus, switch 822 selects sensor 818 during the scans designated a in FIG. 8b. Conversely, when assembly 814 is moving to the left in the x direction as illustrated in FIG. 8a, sensor 818 viewing point 832 is viewing a point which has not yet been heated, while sensor 820 viewing point 834 senses the temperature of the point immediately after heating. Consequently, during scans to the left, switch 822 is set to select the temperature control signal from sensor 820. The scans during which sensor 820 is selected are illustrated as b in FIG. 8b.

Another temperature sensing infrared probe suitable for use in assembly 814 is a type NJL9103 thermopile manufactured by New Japan Radio Co., Ltd. the address of which is Mitsuya Toranomon Bldg. 22-14, Toranomon 1-Chome Minato-ku, Tokyo 105, Japan.

As so far described, the temperature sensor has been an infrared sensor which is capable of sensing substantially only surface temperatures of tissue portion 12. However, the heating effect produced by the power applied to antenna 16 also heats regions below the surface of tissue portion 12, where subcutaneous tumors may be located. While not specifically illustrated, it should be understood that the temperature sensor may be a radiometer generally of the type described in U.S. Pat. No. 4,346,716 issued Aug. 31, 1982, to Carr, modified to use an antenna which radiates effectively in free space. When arranged in a feedback loop, a temperature sensing radiometer may control temperatures within tissue portion 12 rather than controlling temperature near the surface of tissue portion 12.

Other embodiments of the invention will be apparent to those skilled in the art. For example, the antenna for transducing electrical signals into an electromagnetic field for use in air may be replaced by an antenna for transducing electrical signals to an ultrasonic field, which antenna is scanned while both the patient and the antenna are under water for good power transfer efficiency. The scanning may be two-dimensional as described in conjunction with the embodiment, or it may be three-dimensional using a robot arm. The separation of the scan lines of the rectilinear scanning path may be selected based upon the effective size of the heated area. The scan path may be a relatively slow spiral with a rapid radial return, if desired, rather than a rectilinear scan. Antennas other than a simple loop may be used; in particular, a multiturn monofilar or bifilar helix may be used to provide increased antenna gain.

What is claimed is:

1. An apparatus for producing uniform hyperthermic temperature over a large vasculated tissue portion, comprising:

an antenna;

electrical signal generating means coupled to said antenna, the power of said electrical signal generating means being controllable in response to a control signal applied at a control input terminal;

noncontacting temperature indicator means for generating a temperature signal instantaneously indicative of the temperature of tissue within its field of view;

controllable mounting and drive means coupled to said antenna and to said temperature indicator means for recurrently scanning said antenna and said temperature indicator means along a predetermined path over said portion of tissue to be heated whereby said tissue is heated in response to an electromagnetic field produced by said antenna in response to said electrical signal, but said tissue may not be uniformly heated because of variations in the vasculature or field absorption by the tissue, or for other reasons, and said temperature indicator means indicates the temperature of said portion of tissue; and comparator means coupled to said temperature indicator means and to said control input terminal of said electrical signal generating means for comparing said temperature signal with a predetermined signal for generating said control signal for instantaneous control of said power for closing a feedback loop for adjusting said power instant by instant during said scanning for maintaining said tissue at a uniform temperature.

2. An apparatus according to claim 1 wherein said predetermined path is a planar rectilinear scanning path.

3. An apparatus according to claim 2 wherein said antenna is directional and is oriented with the axis of maximum response orthogonal to said planar scanning path and directed towards the surface of said tissue portion.

4. An apparatus according to claim 3 wherein the axis of said field of view of said temperature indicator means is directed parallel to said axis of maximum response.

5. An apparatus according to claim 4 wherein said axis of said field of view of said temperature indicator means coincides with said axis of maximum response.

6. An apparatus according to claim 5 wherein said antenna comprises at least one convolution of conductor having an axis coinciding with said axis of said field of view.

7. An apparatus according to claim 2 wherein said antenna comprises a convolution of conductor centered about an axis and lying in a plane parallel with the plane of said scanning.

8. An apparatus according to claim 7 wherein said temperature indicator means is mounted with said field of view aligned with said axis of said convolution, whereby said temperature indicator means indicates the temperature of that portion of the surface of said tissue on said axis notwithstanding variations in the distance between said surface and said planar scanning path.

9. A method for producing uniform hyperthermia temperature over a large vasculated surface, comprising the steps of:

generating electrical signals;
applying said electrical signals to an antenna;
scanning said antenna over said surface in a predetermined pattern thereby heating said surface by way of the field transduced by said antenna in response to said electrical signals, said heating causing nonuniform surface temperatures due to differences in vasculature and/or differences in field absorption of various portions of said surface;
scanning a noncontacting temperature sensor over said surface in conjunction with said antenna thereby producing a temperature signal indicative of said temperature of said surface during said scanning;
comparing said temperature signal with a reference signal to produce a control signal; and
controlling the power of said electrical signals in response to said control signal to maintain said surface at a uniform temperature.

10. A method according to claim 9 wherein said steps of scanning said antenna over said surface and of scanning said noncontacting temperature sensor over said surface are performed simultaneously.

11. A method according to claim 9 wherein said noncontacting temperture sensor has a field of view along a first axis, and said antenna provides maximum heating of said surface along a second axis, and said steps of scanning said antenna over said surface and of scanning said noncontacting temperture sensor over said surface are performed simultaneously and with said first and second axes coincident.

12. A method for producing uniform hyperthermia temperature in a large vasculated tissue portion, comprising the steps of:

generating electrical signals;
applying said electrical signals to an antenna;
scanning said antenna over the surface of said tissue portion in a predetermined pattern thereby heating said tissue by way of the field transduced by said antenna in response to said electrical signals, said heating causing nonuniform temperatures due to differences in vasculature and/or differences in field absorption of various portions of said tissue;
scanning a noncontacting temperature sensor over said surface in conjunction with said antenna thereby producing a temperature signal indicative of said temperature of said tissue during said scanning;
comparing said temperature signal with a reference signal to produce a control signal; and
controlling the power of said electrical signals in response to said control signal to maintain said tissue at a uniform temperature.

13. A method according to claim 12 wherein said steps of scanning said antenna over said surface and of scanning said noncontacting temperture sensor over said surface are performed simultaneously.

14. A method according to claim 12 wherein said noncontacting temperture sensor has a field of view along a first axis, and said antenna provides maximum heating of said surface along a second axis, and said steps of scanning said antenna over said surface and of scanning said noncontacting temperture sensor over said surface are performed simultaneously and with said first and second axes coincident.

* * * * *